(12) United States Patent
Peter

(10) Patent No.: US 10,010,411 B2
(45) Date of Patent: Jul. 3, 2018

(54) DEVICES AND METHODS FOR PREPARING A TRANSCATHETER HEART VALVE SYSTEM

(71) Applicant: Medtronic Vascular Galway Limited, Ballybrit, Galway (IE)

(72) Inventor: Stephen Peter, Santa Rosa, CA (US)

(73) Assignee: Medtronic Vascular Galway (IE)

( * ) Notice: Subject to any disclaimer, the term of this patent is extended or adjusted under 35 U.S.C. 154(b) by 279 days.

(21) Appl. No.: 15/093,070

(22) Filed: Apr. 7, 2016

(65) Prior Publication Data
US 2016/0220363 A1 Aug. 4, 2016

Related U.S. Application Data

(62) Division of application No. 13/795,917, filed on Mar. 12, 2013, now Pat. No. 9,333,077.

(51) Int. Cl.
*B23P 19/00* (2006.01)
*A61F 2/24* (2006.01)
*A61F 2/00* (2006.01)
*A61F 2/95* (2013.01)

(52) U.S. Cl.
CPC .......... *A61F 2/2415* (2013.01); *A61F 2/0095* (2013.01); *A61F 2/2418* (2013.01); *A61F 2/2427* (2013.01); *A61F 2/2412* (2013.01); *A61F 2/2436* (2013.01); *A61F 2002/9522* (2013.01)

(58) Field of Classification Search
CPC ... B23P 11/00; B23P 6/02; B23P 15/10; B23P 19/10; B23P 19/12
See application file for complete search history.

(56) References Cited

U.S. PATENT DOCUMENTS

| | | | |
|---|---|---|---|
| 5,683,451 A | 11/1997 | Lenker et al. | |
| 5,824,041 A | 10/1998 | Lenker et al. | |
| 5,906,619 A | 5/1999 | Olson et al. | |
| 5,957,949 A | 9/1999 | Leonhardt et al. | |
| 7,105,016 B2 | 9/2006 | Shiu et al. | |
| 8,403,977 B2 | 3/2013 | Case et al. | |
| 9,216,082 B2 * | 12/2015 | Von Segesser | A61F 2/2418 |
| 9,333,077 B2 * | 5/2016 | Peter | A61F 2/2427 |
| 2003/0109886 A1 | 6/2003 | Keegan et al. | |

(Continued)

FOREIGN PATENT DOCUMENTS

| | | |
|---|---|---|
| EP | 1464303 | 10/2004 |
| GB | 2433700 | 7/2007 |

(Continued)

*Primary Examiner* — Lee D Wilson
(74) *Attorney, Agent, or Firm* — Dicke, Billig & Czaja, PLLC

(57) ABSTRACT

Devices and methods for preparing a transcatheter heart valve system. The device includes a housing, sealing apparatuses and a port. The housing forms a chamber sized to receive a prosthetic valve and a portion of a delivery device. During use, the prosthesis is seated in the chamber, and the sealing apparatuses operated to seal the chamber about the delivery device. Air bubbles in a liquid delivered through the delivery device and to the chamber are removed from the system via the port, thereby flushing the system. Further, the device is manipulated to permit loading of the prosthesis into the delivery device in an air bubble-free environment.

7 Claims, 7 Drawing Sheets

(56) References Cited

U.S. PATENT DOCUMENTS

| | | |
|---|---|---|
| 2003/0135970 A1* | 7/2003 | Thornton ............... A61F 2/958 29/270 |
| 2003/0199963 A1 | 10/2003 | Tower et al. |
| 2005/0137688 A1 | 6/2005 | Salahieh et al. |
| 2006/0004439 A1 | 1/2006 | Spenser et al. |
| 2006/0030923 A1 | 2/2006 | Gunderson |
| 2006/0052867 A1 | 3/2006 | Revuelta et al. |
| 2006/0229561 A1 | 10/2006 | Huszar |
| 2006/0259136 A1 | 11/2006 | Nguyen et al. |
| 2006/0265056 A1 | 11/2006 | Nguyen et al. |
| 2007/0005131 A1 | 1/2007 | Taylor |
| 2007/0088431 A1 | 4/2007 | Bourang et al. |
| 2007/0239266 A1 | 10/2007 | Birdsall |
| 2007/0239269 A1 | 10/2007 | Dolan et al. |
| 2008/0065011 A1 | 3/2008 | Marchand et al. |
| 2008/0082165 A1 | 4/2008 | Wilson et al. |
| 2008/0147160 A1 | 6/2008 | Ghione et al. |
| 2008/0147181 A1 | 6/2008 | Ghione et al. |
| 2008/0188928 A1 | 8/2008 | Salahieh et al. |
| 2008/0262590 A1 | 10/2008 | Murray |
| 2009/0018529 A1 | 1/2009 | Hoffman et al. |
| 2009/0054976 A1 | 2/2009 | Tuval et al. |
| 2009/0093876 A1 | 4/2009 | Nitzan et al. |
| 2009/0138079 A1 | 5/2009 | Tuval et al. |
| 2009/0069887 A1 | 6/2009 | Kim et al. |
| 2009/0171447 A1 | 7/2009 | Von Segesser et al. |
| 2009/0177275 A1 | 7/2009 | Case |
| 2009/0281619 A1 | 11/2009 | Le et al. |
| 2009/0299336 A1 | 12/2009 | Jay-Robinson et al. |
| 2010/0094411 A1 | 4/2010 | Tuval et al. |
| 2010/0121434 A1 | 5/2010 | Paul et al. |
| 2011/0098804 A1 | 4/2011 | Yeung |
| 2011/0098805 A1 | 4/2011 | Dwork |
| 2011/0251675 A1 | 10/2011 | Dwork |
| 2011/0251680 A1 | 10/2011 | Tran et al. |
| 2011/0264199 A1 | 10/2011 | Tran |
| 2011/0313354 A1 | 12/2011 | Hennessy |
| 2012/0083876 A1 | 4/2012 | Wang |
| 2012/0330408 A1 | 12/2012 | Hillukka et al. |
| 2014/0277403 A1* | 9/2014 | Peter ............... A61F 2/2427 623/2.11 |
| 2015/0196393 A1* | 7/2015 | Vidlund ............... A61F 2/2439 623/2.11 |

FOREIGN PATENT DOCUMENTS

| | | |
|---|---|---|
| WO | WO2006/076890 | 7/2006 |
| WO | WO2007/071436 | 6/2007 |
| WO | WO2008/138584 | 11/2008 |
| WO | WO2009/091509 | 7/2009 |
| WO | WO2010/120671 | 10/2010 |

* cited by examiner

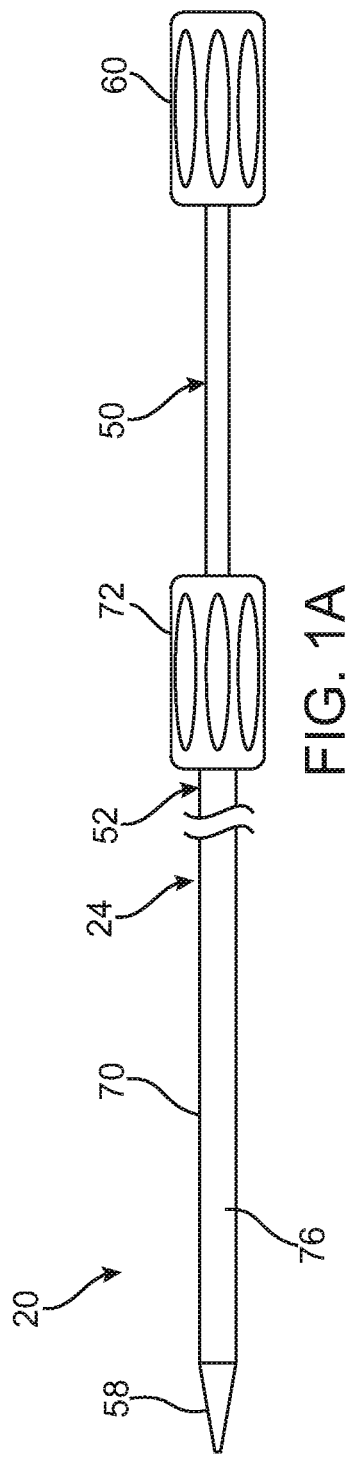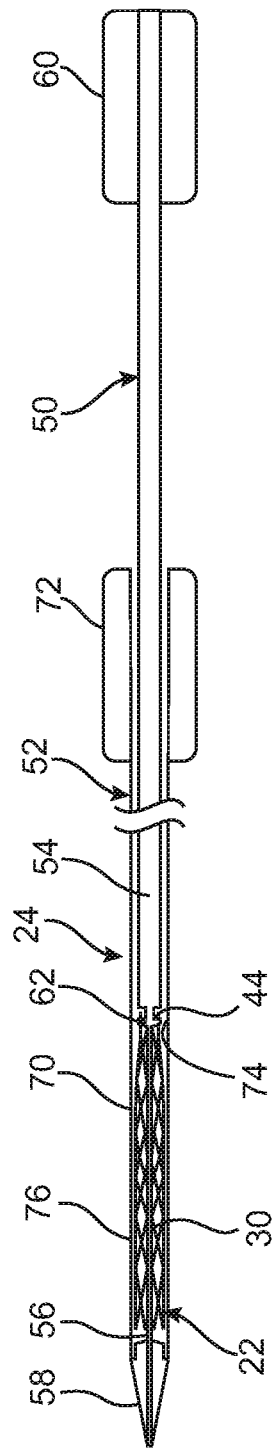
FIG. 1A
FIG. 1B

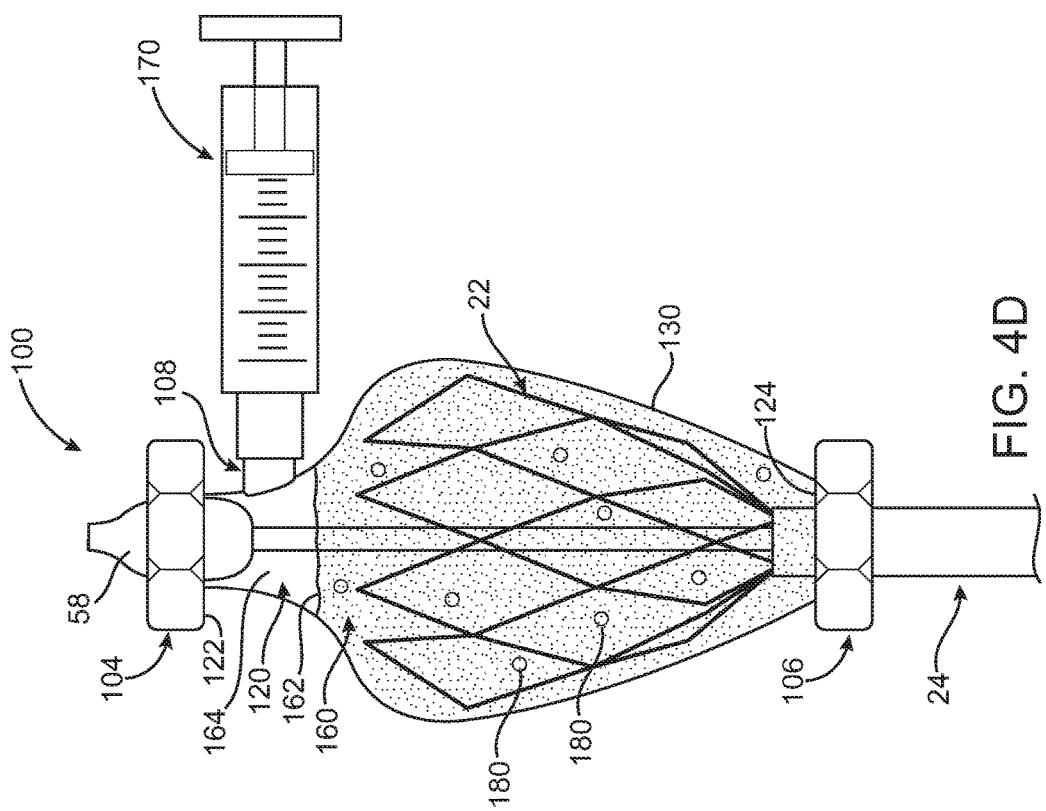
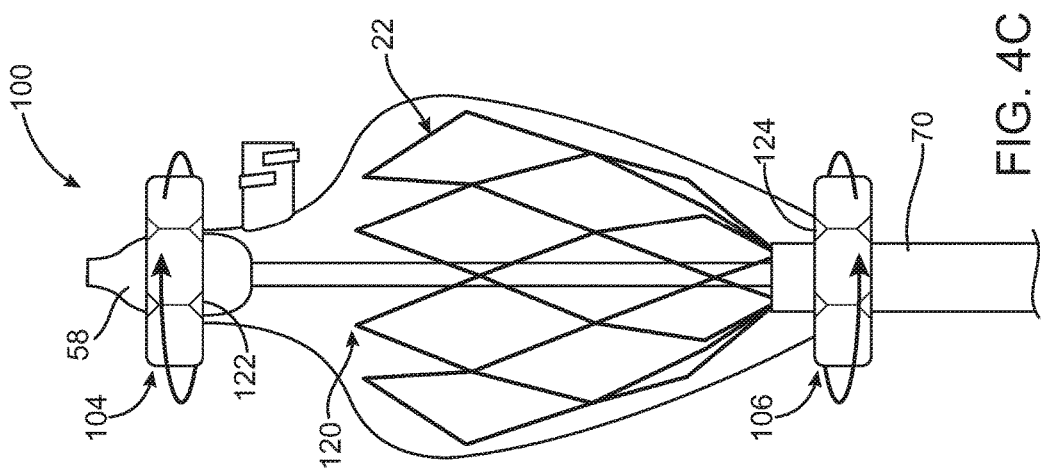

DEVICES AND METHODS FOR PREPARING A TRANSCATHETER HEART VALVE SYSTEM

RELATED APPLICATION

This application is a Division of and claims the benefit of U.S. patent application Ser. No. 13/795,917 filed Mar. 12, 2013, now allowed. The disclosures of which are herein incorporated by reference in their entirety.

BACKGROUND

The present disclosure relates to transcatheter heart valve systems. More particularly, it relates to devices and methods for preparing a transcatheter heart valve system for implanting a stented prosthetic heart valve.

Heart valves, such as the mitral, tricuspid, aortic, and pulmonary valves, are sometimes damaged by disease or by aging, resulting in problems with the proper functioning of the valve. Heart valve problems generally take one of two forms: stenosis in which a valve does not open completely or the opening is too small, resulting in restricted blood flow; or insufficiency in which blood leaks backward across a valve when it should be closed.

Heart valve replacement has become a routine surgical procedure for patients suffering from valve regurgitation or stenotic calcification of the leaflets. Conventionally, the vast majority of valve replacements entail full stenotomy and placing the patient on cardiopulmonary bypass. Traditional open surgery inflicts significant patient trauma and discomfort, requires extensive recuperation times, and may result in life-threatening complications.

To address these concerns, within the last decade, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a prosthetic heart valve is compacted for delivery in a catheter and then advanced, for example through an opening in the femoral artery and through the descending aorta to the heart, where the prosthetic heart valve is then deployed in the valve annulus (e.g., the aortic valve annulus).

Various types and configurations of prosthetic heart valves are used in transcatheter valve procedures to replace defective natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. If bioprostheses are selected, the replacement valves may include a valved vein segment or pericardial manufactured tissue valve that is mounted in some manner within an expandable stent frame to make a valved stent (or stented prosthetic heart valve). In order to prepare such a valve for transcatheter implantation, one type of valved stent can be initially provided in an expanded or uncrimped condition, then crimped or compressed around a balloon portion of a catheter until it is close to the diameter of the catheter. In other transcatheter implantation systems, the stent frame of the valved stent can be made of a self-expanding material. With these systems, the valved stent is crimped down to a desired size and held in that compressed state with a sheath, for example. Retracting the sheath from this valved stent allows the stent to expand to a larger diameter, such as when the valved stent is in a desired position within a patient. With either of these types of percutaneous stent delivery systems, conventional sewing of the prosthetic heart valve to the patient's native tissue is typically not necessary.

The transcatheter delivery system (e.g., the delivery device catheter loaded with a stented prosthetic heart valve) must be free of air bubbles to prevent formation of air embolisms during the implantation procedure. Conventionally, air bubbles are removed by repeatedly flushing the system with a liquid (e.g., saline) to remove air from the system just prior to the implantation procedure. Traditional flushing relies on pushing liquid through the lumen(s) of the delivery device catheter to move bubbles out of the system. This can be difficult with the exceedingly small lumens associated with transcatheter delivery systems, and as the stented prosthetic heart valve is loaded into the catheter, new bubbles can be introduced that are difficult to remove without further flushing.

In light of the above, a need exists for improved devices and methods for preparing transcatheter heart valve systems, including removal of air bubbles.

SUMMARY

Some aspects in accordance with principles of the present disclosure are directed toward an assembly for loading and delivering a stented prosthetic heart valve. The assembly includes a delivery device and a valve loading device. The delivery device can assume a wide variety of forms, and generally includes a tube and a shaft. The tube terminates at a distal end and defines at least one lumen. The shaft is disposed within the lumen and is connected to a tip. The tip, in turn, is located distal the distal end. The valve loading device includes a housing, first and second sealing apparatuses, and a port. The housing forms a chamber and terminates at opposing, first and second ends. An opening to the chamber is defined at both of the ends. The first sealing apparatus is associated with the first end and is configured to selectively sealingly engage the tip. The second sealing apparatus is associated with the second end and is configured to selectively sealingly engage the tube. Finally, the port is open to the chamber. With this construction, the assembly is configured to provide a flushing state in which a stented prosthetic heart valve is seated within the chamber and the valve loading device is assembled to the delivery device. A negative pressure can then be generated in the chamber, and air bubbles removed from the delivered liquid, via the port. In related embodiments, the assembly is configured to provide a loading state in which the chamber is at least partially filled with liquid free of bubbles and the delivery device is operable to load the stented prosthetic heart valve. In other embodiments, the assembly is configured to provide a delivery state in which the valve loading device is removed from the delivery device such that the delivery device can be used to deliver a loaded stented prosthetic heart valve.

Other aspects in accordance with principles of the present disclosure relate to a valve loading device for flushing and loading a transcatheter heart valve system. The transcatheter heart valve system includes a stented prosthetic heart valve and a delivery device. With this in mind, the valve loading device includes a housing, first and second sealing apparatuses, and a port. The housing forms a chamber and terminates at opposing, first and second ends. An opening to the chamber is defined at both of the ends. The first sealing apparatus is associated with the first end and is configured to selectively sealingly engage the delivery device. The second sealing apparatus is associated with the second end and is configured to selectively sealingly engage the delivery. Finally, the port is open to the chamber. The valve delivery device is configured to temporarily retain a stented prosthetic heart valve within the chamber and for temporary assembly to the delivery device such that entrained air bubbles in liquid delivered to the chamber is removed via a negative pressure established through the port. In some embodiments, a check valve is assembled to the port, and the sealing apparatuses each include a Tuohy-Borst valve.

Yet other aspects in accordance with principles of the present disclosure relate to a method of preparing a transcatheter heart valve system including a stented prosthetic heart valve and a delivery device. The method includes seating the stented prosthetic heart valve within a chamber defined by a housing of a valve loading device. In this regard, the housing extends between opposing, first and second ends, and defines an opening to the chamber at each of the ends. A first component of a delivery device is connected to the stented prosthetic heart valve. The first and second openings are sealed relative to the delivery device. A liquid is dispensed through the delivery device and into the chamber. Entrained air bubbles in the so-delivered liquid are removed to flush the delivery device. The stented prosthetic heart valve is captured within the delivery device and the valve loading device is removed from the delivery device. With methods of the present disclosure, a loaded, air bubble-free transcatheter heart valve system is prepared for an implantation procedure. In some embodiments, the housing includes first and second housing sections, with the step of seating the prosthetic heart valve within the chamber including removing the first housing section from the second housing section, locating the prosthesis within the second housing section, and then assembling the first housing section to the second housing section to complete the chamber.

BRIEF DESCRIPTION OF THE DRAWINGS

FIGS. 1A-1C are diagrams illustrating basic components of a transcatheter heart valve system and with which device and methods of the present disclosure are useful;

FIGS. 4A-4E illustrate use of the valve loading device of FIG. 3 in preparing the system of FIG. 1B for an implantation procedure in accordance with principles of the present disclosure.

DETAILED DESCRIPTION

Aspects of the present disclosure relate to devices, and corresponding methods of use, for preparing a transcatheter heart valve system. While an exact configuration of the transcatheter heart valve system components is not critical to features of the present disclosure, the following explanation of an exemplary transcatheter heart valve system can be useful to better understand the devices and methods of the present disclosure.

Figure 1C:
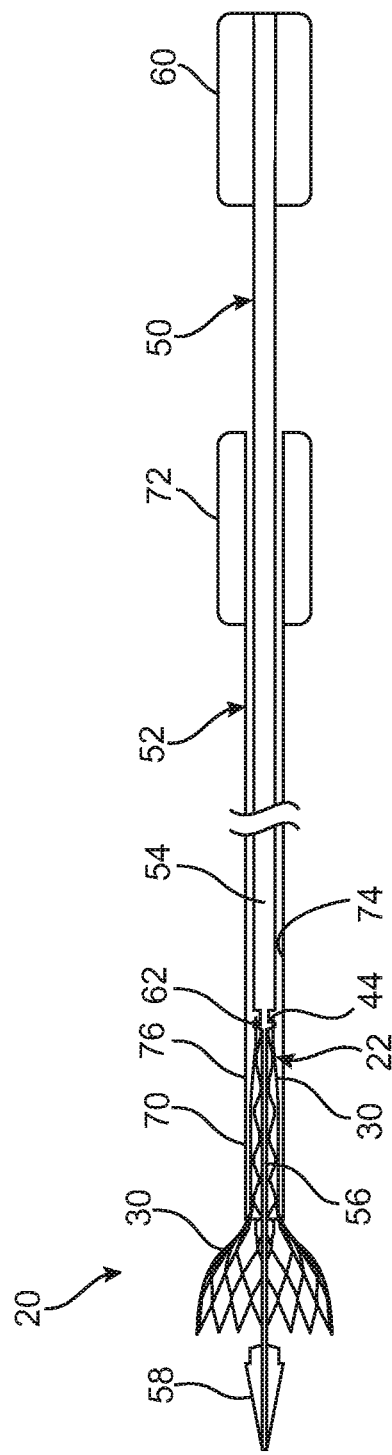

One example of a transcatheter heart valve system 20 with which devices and methods of the present disclosure are useful is shown in simplified form in FIGS. 1A-1C, and includes a stented prosthetic heart valve 22 and a delivery device 24. In general terms, the delivery device 24 is configured to deliver the stented prosthetic heart valve 22 to an implantation site in performing a therapeutic procedure on a defective heart valve of a patient.

Figure 2A:
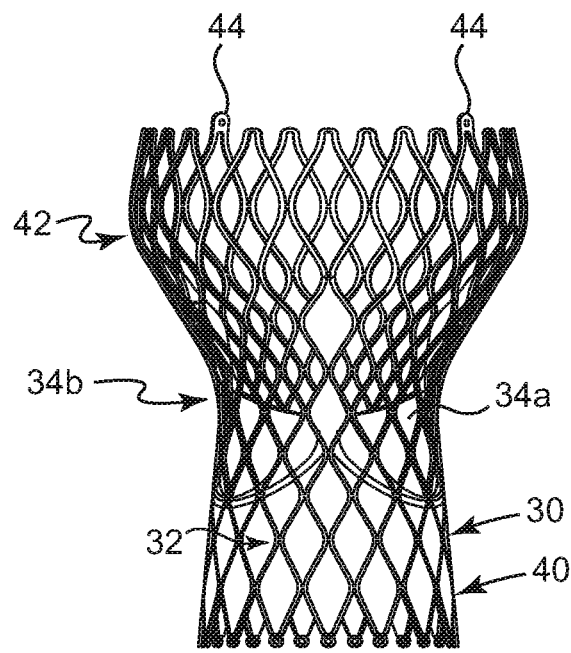
FIG. 2A is a side view of a stented prosthetic heart valve useful with the system of FIGS. 1A-1C and in a normal, expanded arrangement.
Figure 2B:
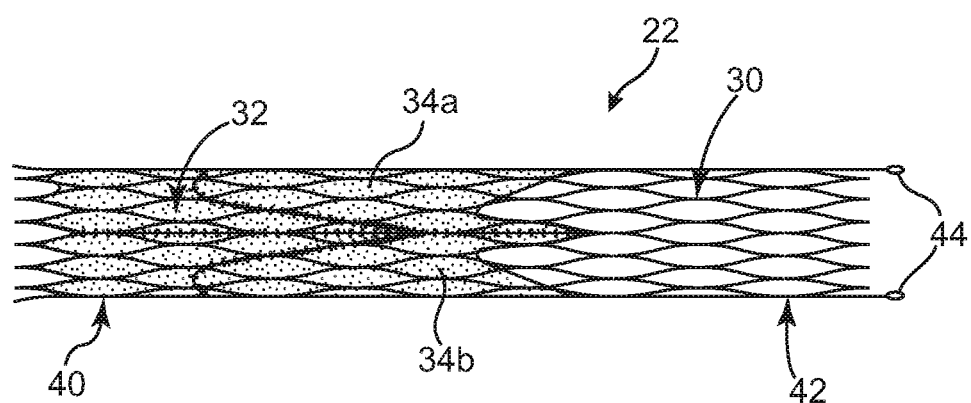
FIG. 2B is a side view of the stented prosthetic heart valve of FIG. 2A in a compressed arrangement.

The stented prosthetic heart valve 22 can assume a wide variety forms. In general terms, and with additional reference to FIGS. 2A and 2B, the stented prosthetic heart valve 22 includes a stent or stent frame 30 and a valve structure 32. The stent frame 30 can be constructed to be self-expandable from a compressed arrangement (FIG. 2B) to a natural, expanded arrangement (FIG. 2A) (e.g., formed of shape memory material such as a nickel titanium alloy). Alternatively, a separate expansion member can be employed (e.g., an expansion balloon). The valve structure 32 forms or provides two or more (typically three) leaflets 34a, 34b. The leaflets 34a, 34b (as well as other portions of the valve structure 32) can be formed from autologous tissue, xenograph material, or synthetics. The leaflets 34a, 34b can be provided as a homogenous, biological valve structure, such as porcine, bovine or equine valves. Alternatively, the leaflets 34a, 34b can be provided independent of one another (e.g., bovine or equine paracardial leaflets) and subsequently assembled to the stent frame 30.

The stented prosthetic heart valve 22 can be viewed as defining an inflow region 40 and an outflow region 42. As a point of reference, "inflow" and "outflow" terminology is in reference to an arrangement of the stented prosthetic heart valve 22 upon final implantation relative to the native valve being repaired or replaced. The valve structure 32 is located along the inflow region 40. The stent frame 30 can form or carry one (or more) connection bodies 44 (e.g., tabs, crowns, posts, etc.) at one or both of the inflow and outflow regions 40, 42 for connection with the delivery device 24 as described below. Non-limiting examples of stented prosthetic heart valves envisioned by the present disclosure are sold under the tradename CoreValve® available from Medtronic CoreValve, LLC, as well as those described in US Publication Nos. 2006/0265056, 2007/0239266 and 2007/0239269, the teachings of which are incorporated herein by reference.

The delivery device 24 can also assume a wide variety of forms, and is generally configured to retain the stented prosthetic heart valve 22 in the compressed arrangement (e.g., FIG. 1B), and selectively release the stented heart valve 22 at the implantation site (partially reflected by FIG. 1C). With this in mind, the delivery device 24 includes a shaft assembly 50 and a sheath assembly 52. The shaft assembly 50 includes a carrier shaft 54 (also referred to as a middle portion or intermediate portion of the shaft assembly 50), a connector shaft 56 (also referred to as a distal portion of the shaft assembly 50), a tip (e.g., a nose cone) 58, and a handle 60. The connector shaft 56 interconnects the carrier shaft 54 and the tip 58, and in some constructions has a reduced outer diameter to permit placement of the stented prosthetic heart valve 22 over the connector shaft 56.

The carrier shaft 54 is sized to be slidably received within a portion of the sheath assembly 52, and is configured in the illustrated embodiments for releasable coupling with the stented prosthetic heart valve 22. For example, the carrier shaft 54 can form or including a coupling body 62 configured to selectively engage a corresponding feature of the stented prosthetic heart valve 22, for example the connection bodies 44 described above.

The tip 58 can assume a variety of formats, and is generally constructed to facilitate atraumatic placement of the transcatheter valve system 20 through a patient's vasculature and heart. The handle 60 is mounted or connected to a proximal end of the carrier shaft 54, and provides a convenient surface for grasping by a clinician.

The sheath assembly 52 generally includes at least one tube or sheath 70 and a handle 72. The tube 70 can be of a conventional catheter-like configuration (e.g., biocompatible polymer with or without an encapsulated wire braiding) and forms at least one lumen 74. The lumen 74 is sized to slidably receive the carrier shaft 54 as well as the stented prosthetic heart valve 22 in the collapsed arrangement. In some constructions, the tube 70 can be constructed of two (or more) sections, including a reinforced capsule or capsule section 76 configured to retain the stented prosthetic heart valve 22 in the compressed arrangement. Regardless, the tube 70 is generally compliant, and is able to traverse the tortuous pathways associated with transcatheter heart valve implantation. The handle 72 can assume a wide variety of forms, and is generally mounted or connected to a proximal end of the tube 70. Though not shown, a flush port is provided with one or both of the handles 60, 72 for delivering a flushing liquid into the tube 70 at least in a region of the capsule 76.

The delivery device 24 is operable to deliver or implant the stented prosthetic heart valve 22 as follows. FIGS. 1A and 1B illustrate the transcatheter valve system 20 in a loaded state, including the stented prosthetic heart valve 22 fully contained within the tube 70 of the delivery device 24, prior to deployment. For example, the stented prosthetic heart valve 22 is connected to the carrier shaft 54 (e.g., engagement between the connection bodies 44 and the coupling body 62), and is radially constrained within the tube 70. The delivery device 24 is configured to transition from the loaded state in which the tube 70 encompasses the stented prosthetic heart valve 22 to a deployed state in which the tube 70 is withdrawn from the stented prosthetic heart valve 22.

For aortic valve replacement procedures, the transcatheter valve system 100 is, in the loaded state, advanced toward the implantation target site, for example in a retrograde manner through a cut-down in the femoral artery and into the patient's descending aorta. The system 10 is then advanced, under fluoroscopic guidance, over the aortic arch, through the ascending aorta, and midway across the defective aortic valve. The tube 70 is partially retracted relative to the stented prosthetic heart valve 22 as shown in FIG. 1C. For example, the handle 72 provided with the sheath assembly 52 is retracted toward the handle 60 of the shaft assembly 50. As shown, a portion of the stent 30 is thus exteriorly exposed relative to the tube 70 and begins to self-deploy. This proximal retraction of the tube 70 continues, with a continually increasing length of the stented prosthetic heart valve 22 being exposed and thus partially deployed, until the prosthesis 22 is fully deployed in the native valve.

As indicated above, the stented prosthetic heart valve 22 is loaded within the delivery device 24 in a loaded state of the transcatheter heart valve system 20. Any air bubbles in the lumen 74 should be removed prior to the implantation procedure. The devices and methods of the present disclosure are useful in accomplishing both steps.

Figure 3:
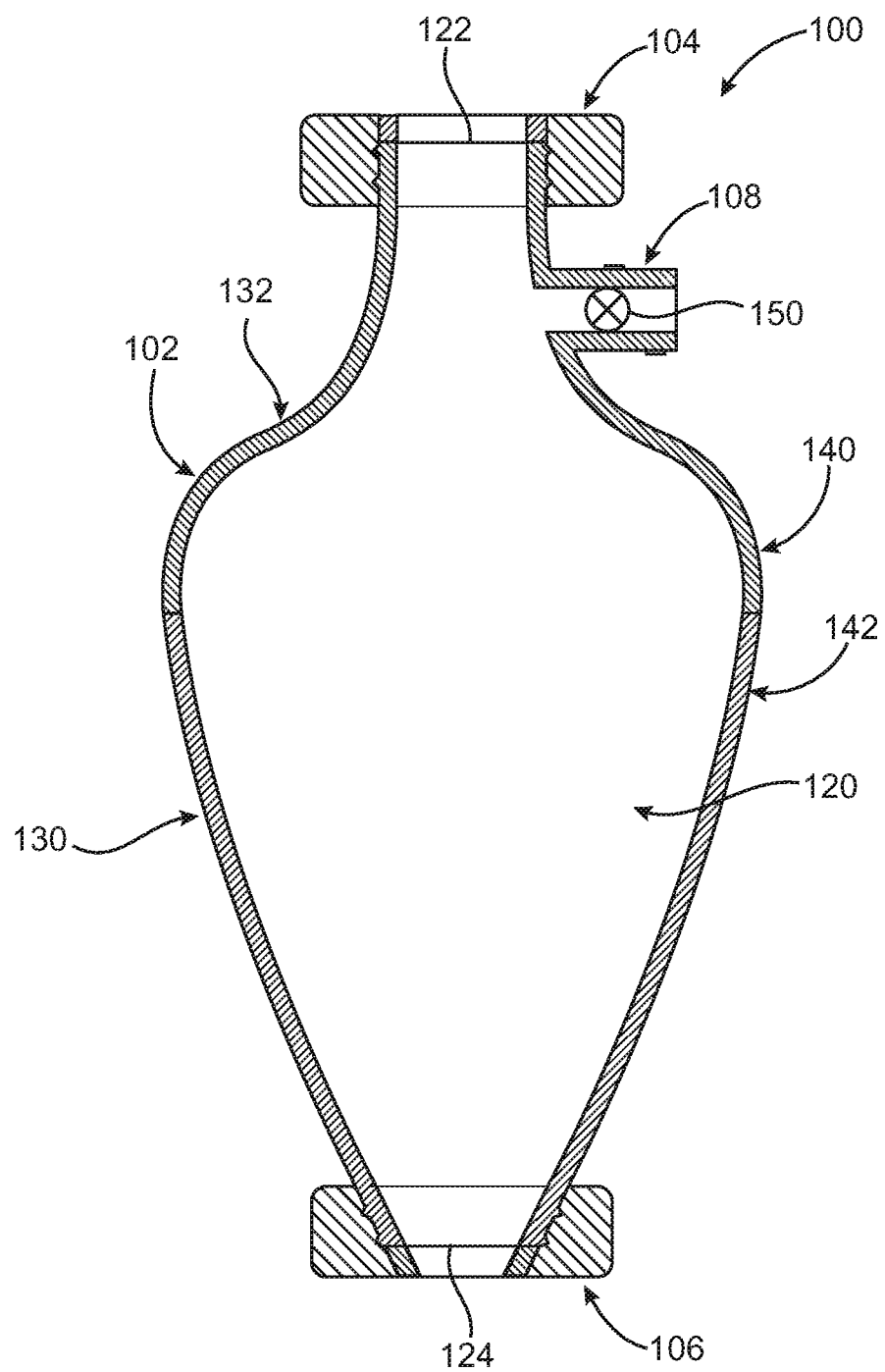
FIG. 3 is a simplified cross-sectional view of a valve loading device in accordance with principles of the present disclosure.

One embodiment of a loading device 100 in accordance with principles of the present disclosure is shown in FIG. 3 and includes a housing 102, a first sealing apparatus 104, a second sealing apparatus 106, and a port 108. Details on the various components are provided below. In general terms, the housing 102 is configured to receive a stented prosthetic heart valve (e.g., any of the stented prosthetic heart valves 22 (FIG. 2A) described above), and the sealing apparatuses 104, 106 are configured to selectively establish a liquid-tight seal with components of a delivery device (e.g., any of the delivery devices 24 (FIG. 1B) described above). The port 108 provides a conduit through which a vacuum can be drawn within the housing 102 as part of a flushing operation. Following flushing, the loading device 100 promotes loading of the stented prosthetic heart valve to the delivery device in an environment free of air bubbles.

The housing 102 is relatively rigid (e.g., hardened plastic or metal) and defines a chamber 120. The housing 102 extends between opposing, first and second ends 122, 124, and defines an opening to the chamber 120 at each of the ends 122, 124. In some embodiments, the housing 102 forms the chamber 120 to have a size and shape corresponding with a size and shape of the stented prosthetic heart valve (not shown) to be utilized with the loading device 100. For example, the housing 102 can be characterized as defining a prosthesis segment 130 and a neck segment 132. The prosthesis segment 130 extends from the second end 124 and forms the corresponding portion of the chamber 120 to have an increasing diameter in a direction of the first end 122 (e.g., the prosthesis segment 130 can have a funnel-like shape). With additional reference to FIG. 2A, a size and shape of the prosthesis segment 130 generally corresponds with that of the stented prosthetic heart valve 22 in, or near, the normal, expanded arrangement. More particularly, the diameter of the chamber 120 along the prosthesis segment 130 approaches or approximates the diameter of the outflow region 42 of the stented prosthetic heart valve 22 in the normal, expanded arrangement. Conversely, a diameter of the prosthesis segment 130 at least immediately adjacent the second end 124 is less than a diameter of the stented prosthetic heart valve 22 in the normal, expanded arrangement. As made clear below, then, the chamber 120 can be configured to effectuate partial collapse or crimping of the stented prosthetic heart valve 22 at the second end 124 and along a portion of the prosthesis segment 130 immediately adjacent the second end 124.

The neck segment 132 extends from the prosthesis segment 130, and has a reduced or tapering diameter in a direction of the first end 122 in some embodiments. Because the chamber 120 is sized and shaped to receive a majority, alternatively an entirety, of the stented prosthetic heart valve 22 within the prosthesis segment 130, the reduced diameter of the neck segment 132 does not affect substantial, if any, collapse or crimping of the stented prosthetic heart valve 22 as described below.

In some embodiments, the housing 102 consists of two (or more) housing sections 140, 142. The housing sections 140, 142 can take various forms, and are configured to be selectively assembled to, and disassembled from, one another, and collectively define the chamber 120 upon final assembly. In this regard, the valve loading device 100 can include one or more additional components that maintain a liquid-tight seal between the housing sections 140, 142 upon final assembly (e.g., one or more gaskets, fasteners, etc.).

Further, the housing sections 140, 142 can include various complimentary features that promote mated assembly.

The first sealing apparatus 104 is associated with the first end 122 of the housing 102 (e.g., is assembled to the housing 102 at or immediately adjacent the first end 122) and is configured to selectively seal the opening at the first end 122 relative to a corresponding component of the delivery device 22 (FIG. 1B) as described below. The second sealing apparatus 106 is similarly associated with the second end 124 of the housing 102 (e.g., is assembled to the housing 102 at or immediately adjacent the second end 124) and is configured to selectively seal the opening at the second end 124 relative to a corresponding component of the delivery device 22 as described below.

In some embodiments, the first and second sealing apparatuses 104, 106 can be identical, and each includes a valve (not shown). The valve can be a hemostasis valve and in some embodiments is a Tuohy-Borst valve. Other valve constructions, such as a duckbill valve, a pinhole valve, a slit valve, etc., are also envisioned. In some constructions, one or both of the sealing apparatuses 104, 106 include a mechanism or structure that allows a user to selectively actuate and release the valve relative to the corresponding delivery device component.

For reasons made clear below, in some embodiments the port 108 is located along the neck segment 132. Regardless, the port 108 is fluidly open to the chamber 120. In some embodiments, a check valve 150 (e.g. a Luer-lock adaptor) is provided with, or forms, the port 108.

Figure 4B:
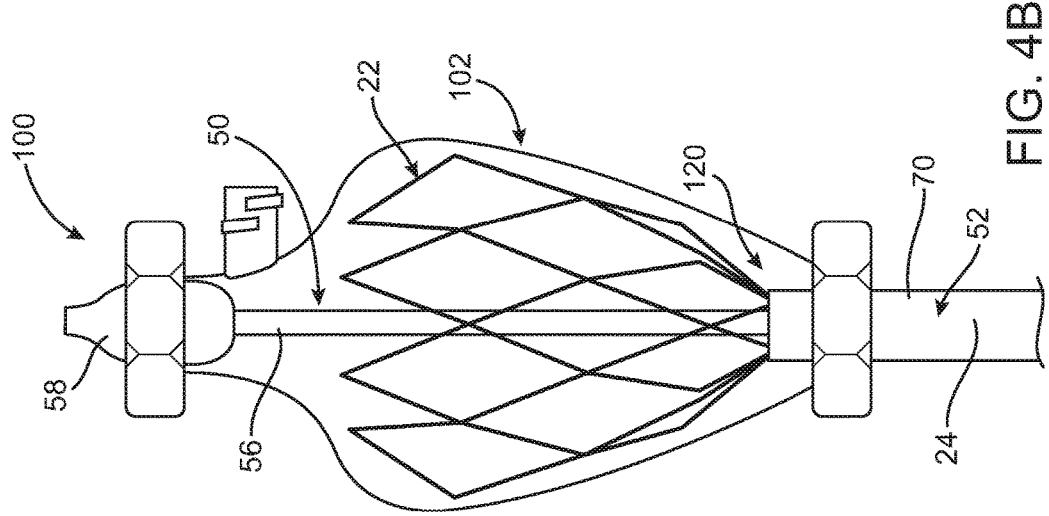
Figure 4A:
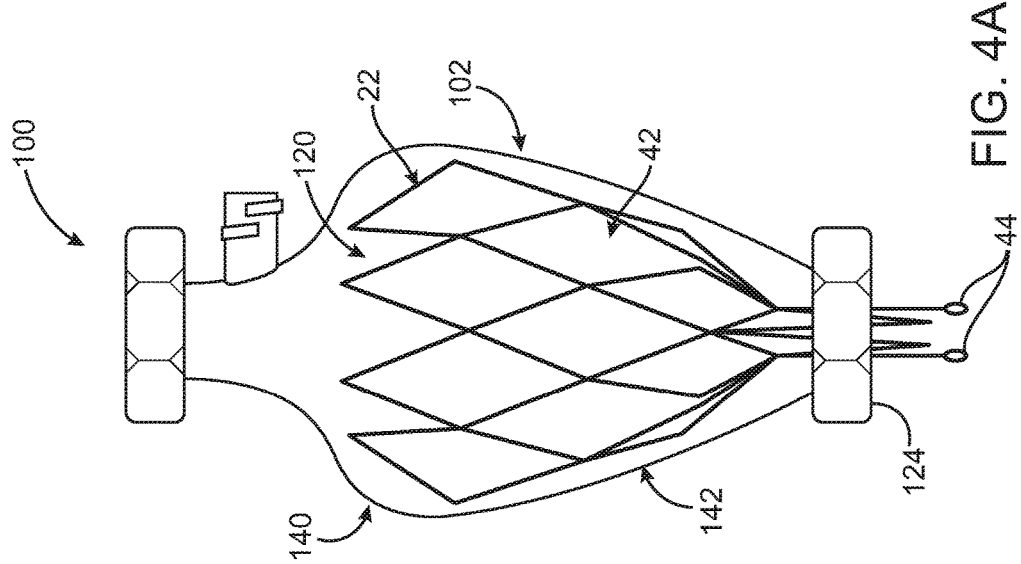

Use of the valve loading device 100 in performing a transcatheter heart valve system flushing and loading operation initially includes seating the stented prosthetic heart valve 22 within the chamber 120 as generally reflected in FIG. 4A. As a point of reference, the housing 102 is illustrated as being transparent in the view of FIGS. 4A-4E to show an interior thereof. Placement of the stented prosthetic heart valve 22 can be accomplished in various fashions as a function of the particular configuration of the housing 102. For example, where the housing 102 includes the first and second housing section 140, 142, the first housing section 140 can initially be removed from the second housing section 142, allowing the stented prosthetic heart valve 22 to be more easily inserted into the second housing section 142. The first housing section 140 is then assembled to the second housing section 142 to complete the housing 102. Regardless, and as generally reflected by FIG. 4A, in some embodiments the chamber 120 is sized and shaped such that only portion of the stented prosthetic heart valve 22 is forced to or toward a collapsed arrangement (e.g., the outflow region 42), whereas other portions of the prosthesis 22 are subjected to lessened, if any, compressive forces. The connection bodies 44 provided with the stented prosthetic heart valve 22 extend beyond, or are otherwise accessible at, the second end 124.

The delivery device 24 is then connected to the stented prosthetic heart valve 22 as shown in FIG. 4B. In particular, the shaft assembly 50 is distally advanced relative to sheath assembly 52, locating the tip 58 distally beyond the stented prosthetic heart valve 22. The connector shaft 56 is located within the chamber 120, and the delivery device 24 captures the connection bodies 44 (FIG. 4A) of the prosthesis 22. For example, though hidden in the view of FIG. 4B, the connection bodies 44 are forced into captured engagement with the coupling body 62 (FIG. 1B) within the tube 70.

With reference to FIG. 4C, the first sealing apparatus 104 is then operated to establish a liquid-tight seal with the tip 58, and the second sealing apparatus 106 is operated to establish a liquid-tight seal with an exterior surface of the tube 70. Thus, the chamber 120 is sealed at the openings of the first and second housing ends 122, 124 (but is open to the lumen 74 (FIG. 1B) of the tube 70), and encloses the stented prosthetic heart valve 22.

A flushing operation is then performed as reflected by FIG. 4D. Saline or other liquid 160 (referenced generally) is delivered through the lumen 74 (FIG. 1B), for example via a flush port or similar assembly (not shown) located at a proximal side of the delivery device 24. The liquid 160 traverses through the lumen 74 and enters the chamber 120. With the valve loading device 100 in the upright orientation shown in FIG. 4D, the liquid 160 fills a substantial volume, but not an entirety, of the chamber 120. A fill line 162 of the liquid 160 is established above or beyond the prosthesis 22 but below the port 108. Thus, an air cavity 164 is generated, with the port 108 being fluidly open to the air cavity 164. The proximal side flush port(s) is then closed and a vacuum instrument 170 is assembled to the port 108. The vacuum instrument 170 can assume a variety of forms, for example a syringe, and can be considered a component of the valve loading device 100. The vacuum instrument 170 is operated to establish a negative pressure or vacuum in the chamber 120. The negative pressure causes a volumetric expansion of the air within the chamber 120 and thus a pressure drop in the chamber 120 and the delivery device lumen 74. This pressure drop, in turn, facilitates removal of air bubbles 180 from the liquid 160. Typically, this is seen as smaller air bubbles in the system 20 expand under the reduced pressure, sometimes coalesce with other nearby air bubbles, and move through the system 20 and into the air cavity 164. The check valve 150 (FIG. 3) prevents liquid (and possibly air bubbles) from flowing back into the chamber 120 from the vacuum instrument 170.

Figure 4E:
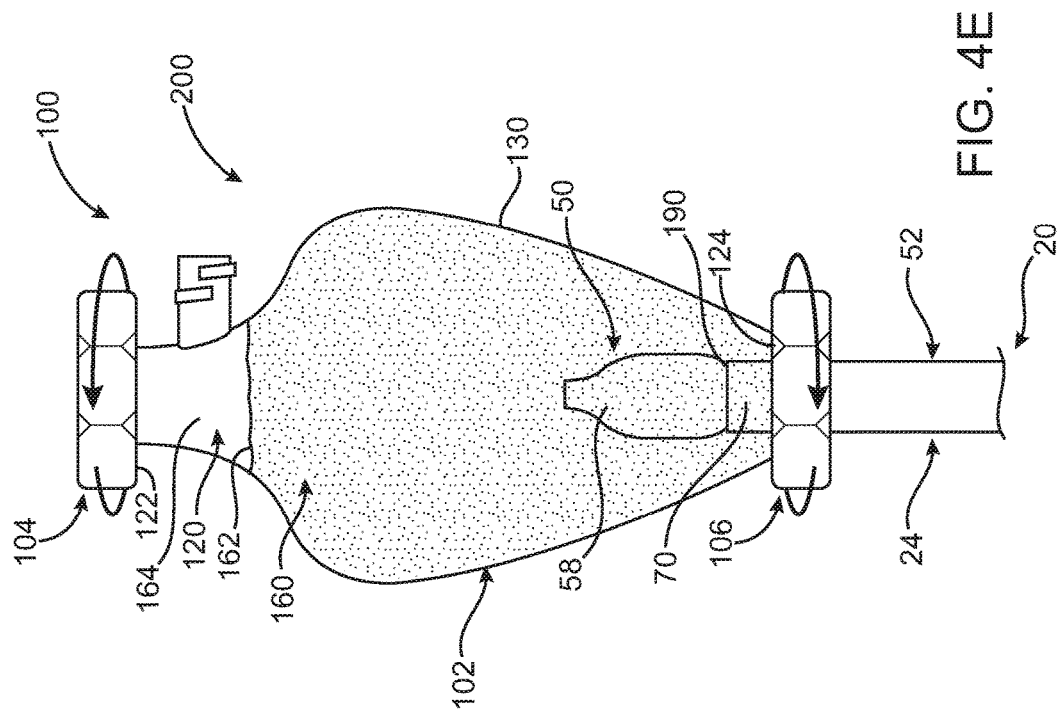

Once the clinician is satisfied that the air bubbles 180 have been sufficiently flushed, the transcatheter heart valve system 20 is transitioned to the loaded state. The chamber 120 remains substantially filled with the liquid 160 (but is now free of the air bubbles 180), with the fill line of the liquid 160 being beyond the prosthesis 22. The first sealing apparatus 104 is slightly released relative to the tip 58. As shown in FIG. 4E, the shaft assembly 50 (referenced generally) can then be retracted relative to the sheath assembly 52, bringing the stented prosthetic heart valve 22 (hidden in FIG. 4E) fully within the tube 70. The tapered shape of the prosthesis segment 132 assists in "funneling" the prosthesis 22 into the tube 70. Alternatively, the second sealing apparatus 106 can be slightly released relative to the tube 70 and the sheath assembly 52 advanced. As shown, the tip 58 has moved proximally into abutment with a distal end 190 of the tube 70. The valve loading device 100 can then be removed from the delivery device 24, with the transcatheter heart valve system 20 (referenced generally) now in the loaded state and properly prepared for an implantation procedure.

Because the valve loading device 100 is configured in accordance with corresponding features of the delivery device 24 to effectuate the liquid-tight seals described above, in some embodiments the present disclosure can be viewed as providing a flushing and loading assembly 200 that includes the delivery device 24 and the valve loading device 100. In a flushing state of the assembly 200, the valve loading device 100 is mounted to the delivery device 24, including liquid-tight sealed engagement at the first and second ends 122, 124 of the housing 102 as described above. In a loading state of the assembly 200, the valve loading device 100 remains connected to the delivery device 24, but in a manner permitting manipulation of the delivery device

24 in loading the stented prosthetic heart valve 22 into the delivery device. Finally, in a delivery state of the assembly 200, the valve loading device 100 is entirely removed from the delivery device 24 so that the delivery device 24 is available to perform valve implantation.

Devices, assemblies and methods of the present disclosure provide a marked improvement over previous designs. Removal of air bubbles from a transcatheter heart valve system is readily performed by creating a negative pressure or vacuum in the system (as compared to conventional techniques whereby flushing relies solely upon the flushing liquid being pushed through the system). Further, an air bubble-free, liquid immersed environment is created in which the stented prosthetic heart valve can be loaded into the delivery device's capsule, sheath or other tube, thereby minimizing the possibility that new air bubbles will be generated during loading.

Although the present disclosure has been described with reference to preferred embodiments, workers skilled in the art will recognize that changes can be made in form and detail without departing from the spirit and scope of the present disclosure.

What is claimed is:

1. A method of preparing a transcatheter heart valve system, including a delivery device and a stented prosthetic heart valve, for the performance of a transcatheter valve implantation procedure, the method comprising:
    seating a stented prosthetic heart valve within a chamber defined by a housing of a valve loading device, the housing extending between opposing, first and second ends and defining an opening to the chamber at the each of the first and second ends;
    connecting a first component of a delivery device to the stented prosthetic heart valve;
    sealing the first and second openings relative to the delivery device;
    dispensing a liquid through the delivery device and into the chamber;
    creating a negative pressure in the chamber to remove air bubbles entrained in the liquid;
    capturing the stented prosthetic heart valve within the delivery device; and
    removing the valve loading device from the delivery device.

2. The method of claim 1, wherein the delivery device further includes a tube defining a lumen and a shaft disposed within the lumen, the shaft connect to a tip located distal the tube, and further wherein the step of sealing the first and second openings includes establishing a seal at the tip and a seal at the tube.

3. The method of claim 2, wherein the first component is a coupling body, carried by the shaft and configured to mate with a corresponding component of the stented prosthetic heart valve.

4. The method of claim 3, wherein the step of capturing the stented prosthetic heart valve within the delivery device includes:
    releasing the seal at the tip; and
    retracting the shaft relative to the tube to draw the stented prosthetic heart valve into the lumen.

5. The method of claim 2, wherein the stented prosthetic heart valve is configured to be reversibly collapsible from a natural arrangement to a collapsed arrangement, and further wherein:
    following the step of loading the stented prosthetic heart valve within the chamber and during the step of dispensing a liquid, at least a portion of the stented prosthetic heart valve is distally beyond the tube and has a diameter greater than a diameter of the lumen; and
    following the step of capturing the stented prosthetic heart valve within the delivery device, the stented prosthetic heart valve is retained in the collapsed arrangement, including an entirety of the prosthetic heart valve having a diameter not greater than a diameter of the lumen.

6. The method of claim 1, wherein the loading device further includes a port open to the chamber, and further wherein the step of establishing a negative pressure in the chamber includes operating a vacuum instrument connected to the port, the port being located distal the stented prosthetic heart valve.

7. The method of claim 1, wherein the housing includes first and second housing section, and further wherein the step of seating the stented prosthetic heart valve within the chamber includes:
    loading the stented prosthetic heart valve within the second housing section, including the first housing section being separated from the second housing section; and
    assembling the first housing section to the second housing section to complete the chamber.

\* \* \* \* \*